United States Patent [19]

Glaser et al.

[11] Patent Number: 4,586,510

[45] Date of Patent: May 6, 1986

[54] APPARATUS FOR EXERCISING A PARALYZED LIMB

[75] Inventors: Roger M. Glaser; Marcus Glaser; Steven R. Collins; Jonathan R. Strayer, all of Dayton, Ohio

[73] Assignee: Wright State University, Dayton, Ohio

[21] Appl. No.: 635,314

[22] Filed: Jul. 27, 1984

[51] Int. Cl.$^4$ .............................................. A61N 1/36
[52] U.S. Cl. ............................... 128/423 W; 128/795; 272/134; 272/117
[58] Field of Search ......... 272/117, 125, 134, DIG. 5, 272/DIG. 6; 128/795, 423 W

[56] References Cited

U.S. PATENT DOCUMENTS

| | | | |
|---|---|---|---|
| 1,498,529 | 6/1924 | Allen | 128/796 |
| 4,177,819 | 12/1979 | Kofsky et al. | 128/422 |
| 4,392,496 | 7/1983 | Stanton | 128/423 W |
| 4,480,830 | 11/1984 | Petrofsky et al. | 272/117 |
| 4,499,900 | 2/1985 | Petrofsky | 128/423 W |

OTHER PUBLICATIONS

U.S. Patent Application Ser. No. 417,935 filed Sep. 14, 1982, Petrofsky et al.
"A System for Evaluation and Exercise-Conditioning of Paralyzed Leg Muscles", Gruner et al., Journal of Rehabilitation R & D, vol. 20, No. 1, 1983, (BPR 10–38), pp. 21–30.

Primary Examiner—Richard C. Pinkham
Assistant Examiner—Leo P. Picard
Attorney, Agent, or Firm—Biebel, French & Nauman

[57] ABSTRACT

A system for exercising paralyzed human limbs by functional electrical stimulation. The system utilizes simple analog devices including a reference signal generator, a position sensor and an error signal generator. The error signal is integrated to produce a stimulation driving signal for application to stimulation electrodes mounted on the limb. In the disclosed embodiment the paralyzed person may be seated in an exercise chair. The chair is equipped with a pair of loading assemblies which may be attached to the legs of the person so as to yieldingly resist stimulated movement thereof.

10 Claims, 6 Drawing Figures

APPARATUS FOR EXERCISING A PARALYZED LIMB

BACKGROUND OF THE INVENTION

This invention relates to apparatus for directing coordinated movement of paralyzed muscles and exercising them to reverse the atrophy resulting from the inactivity which follows the onset of a paralyzing occurrence. A typical prior art device is shown, for instance, in Petrofsky et al Ser. No. 417,935, filed Sept. 14, 1982. Through the use of such devices it has been found possible to exercise paralyzed muscles in a controlled fashion, even after years of inactivity. Such systems operate by applying electrical stimulation to muscles which have been cut off from communication with the brain, as a result of spinal cord damage, stroke, or other neuromuscular conditions involving upper motoneuron dysfunction.

A system as taught by Petrofsky et al includes a microprocessor for generating digital commands indicating a desired motion by a paralyzed limb, a digital-to-analog converter, a plurality of stimulation electrodes, a sensor for sensing motion of the stimulated limb, and an analog-to-digital converter which receives the output of the position sensor and converts it to digital form for use by the microprocessor. The system also includes dynamic load means which apply a resisting force to the paralyzed limb during stimulated motion thereof.

While a system as taught by Petrofsky et al is able to perform numerous complex mathematical manipulations as appropriate for carrying out a variety of sophisticated exercise routines, there exists a need for a simpler device which need not be programmed and which is able to conduct a specified exercise routine for a paralyzed limb, such as a human leg.

SUMMARY OF THE INVENTION

This invention provides an effective system based upon simple anlog devices for exercising a paralyzed limb by functional electrical stimulation. The system includes means for generating a reference signal indicating a range of desired limb positions varying from a rest position to a working position and then back to the rest position, and a position sensor for sensing the position of the limb and generating a corresponding position signal. A differential amplifier compares the reference signal with the position signal and generates an error signal representing the observed difference. The error signal is integrated by a stimulus integrator to produce a stimulation driving signal for application to stimulation electrodes mounted on the limb. This stimulates muscular activity in the limb and causes controlled movement thereof from the rest position to the working position and back to the rest position. A loading device, which may comprise a simple weight, resists the movement of the limb to produce muscular exertion.

In preferred embodiment the reference signal is generated by means including a timer which generates a timing signal progressing from a level quiescent value to a timing pulse of predetermined duration and back to the quiescent value. The timing signal is integrated by a reference integrator to produce the reference signal. Such integration of the timing signal produces a reference signal which ramps from a rest value to a working value and then reversly to the rest value. Also in preferred embodiment, the stimulation driving signal is chopped into a pulsatile output signal for application to the stimulation electrodes.

A system constructed in accordance with this invention is relatively inexpensive to produce, easy to operate and fully effective. Desired exercise performance parameters during a contraction cycle may be set by simply turning adjustment potentiometers which control stimulation threshold level, rate of limb extension, target angle of limb extension, time to hold the target angle, and rate of limb return to resting position. Once these parameters are set it is only necessary to trigger the stimulator to cause it to go through its complete contraction cycle sequence. A momentary switch is provided for initiating subsequent contraction cycles. Alternatively, there may be provided a pair of such stimulation units connected to an automatic switching unit through a pair of isolation amplifiers. This permits automatic alternate triggering of contraction cycles for exercising a pair of paralyzed limbs.

Accordingly, it is an object of the present invention to exercise a paralyzed limb through use of a simplified functional electrical stimulation system.

Other objects and advantages of the present invention will be apparent from the following description, the accompanying drawings and the appended claims.

DESCRIPTION OF THE PREFERRED EMBODIMENT

Figure 1:
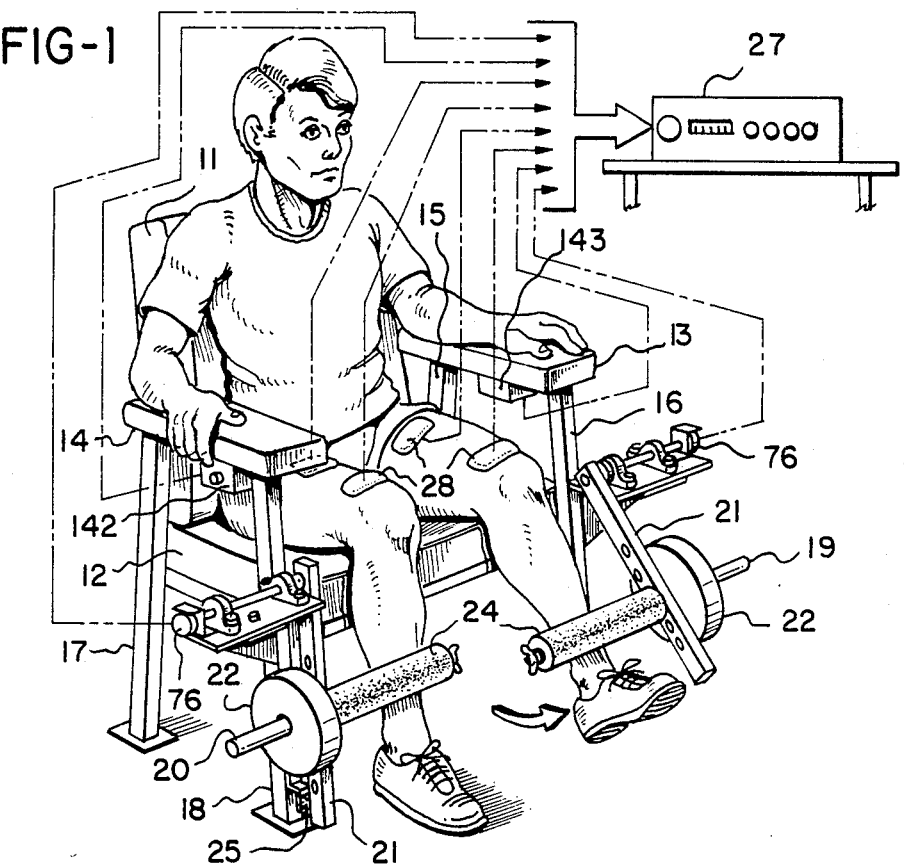
FIG. 1 is a pictorial sketch illustrating a complete system constructed in accordance with this invention.
Figure 3A:
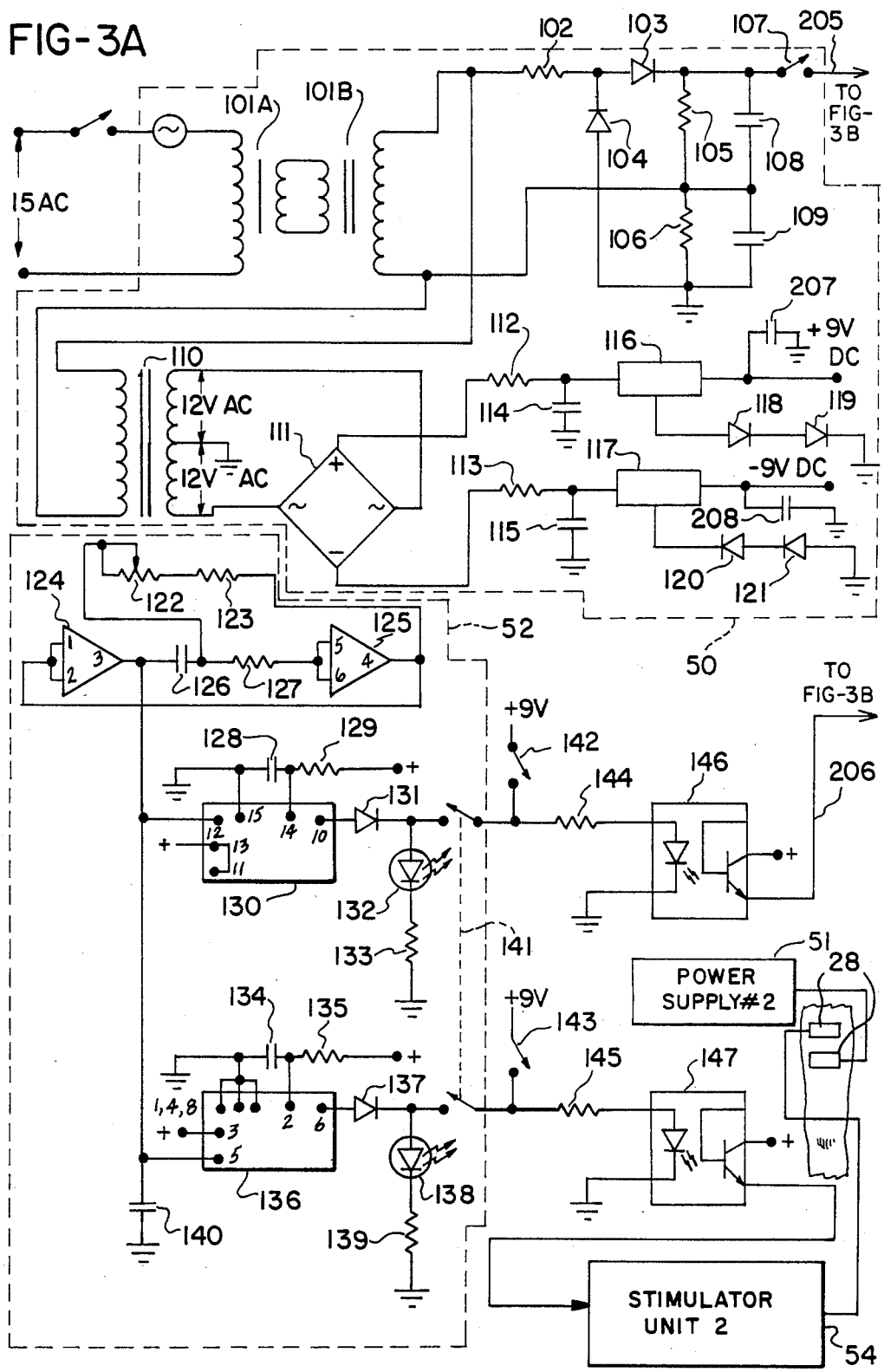
FIGS. 3A and 3B are an electrical schematic diagram of a pair of stimulator units built in accordance with this invention and connected to a remote control unit.
Figure 3B:
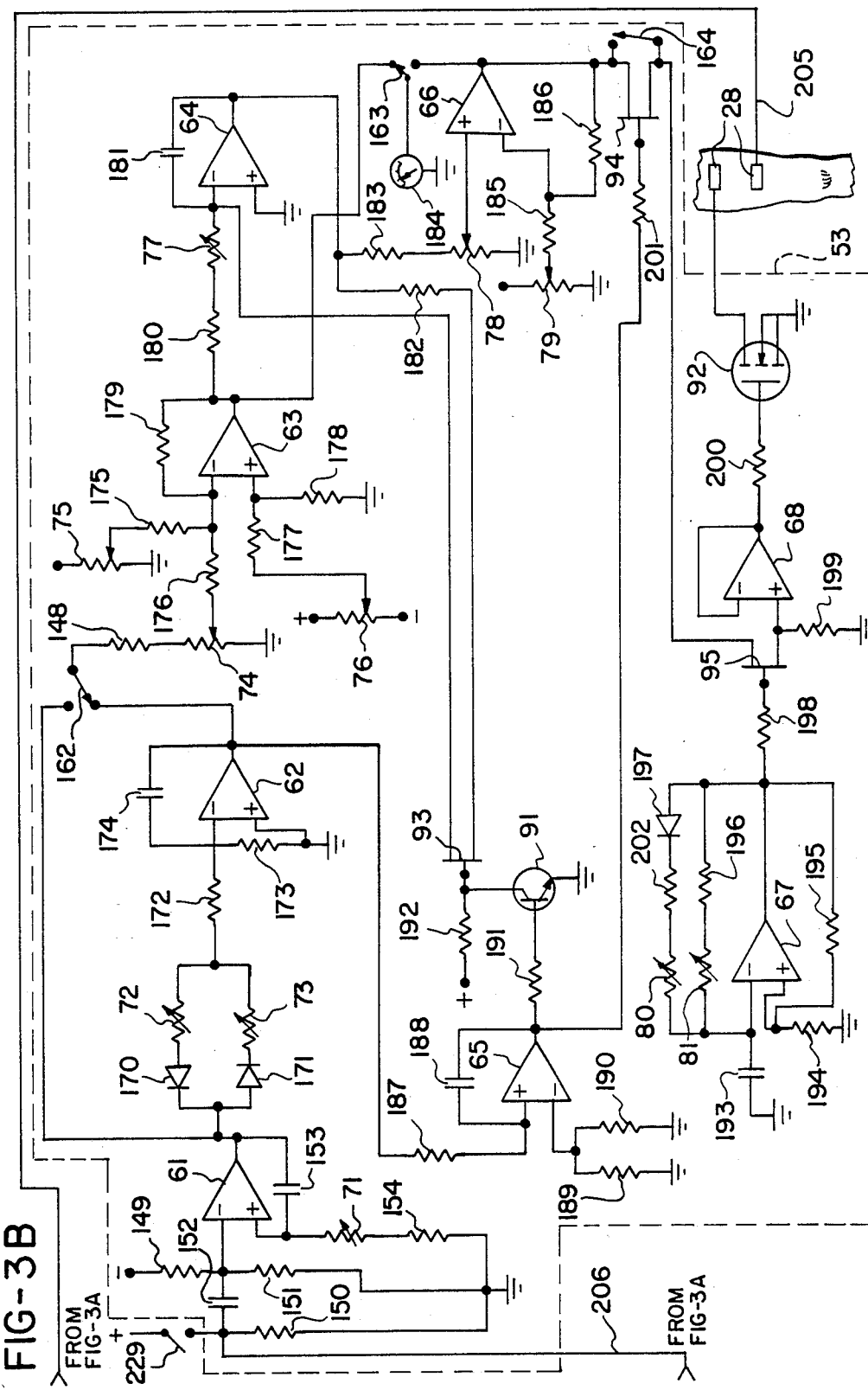

Apparatus in accordance with the present invention may be utilized as generally illustrated in FIG. 1 and may be configured electrically as illustrated in FIGS. 3A and 3B. TABLE I identifies the components depicted in the figures.

As illustrated in FIG. 1 a paralyzed person who desires electrically induced stimulation of his quadriceps muscles may sit in a chair 10 including a chair back 11, a seat 12, left and right arm rests 13 and 14 and legs 15 through 18. A pair of limb loading assemblies 19 and 20 may be pivotally supported by chair legs 16 and 18, respectively, for stimulated exercising of the patient's left and right legs. Each limb loading assembly includes a support arm 21 pivotally supported at its upper end by an extension of its associated chair leg. Support arm 21 carries a spindle 23 upon which are mounted a cylindrical cushion member 24 and an annular weight 22. The weight 22 is selected to provide the desired amount of resistance against leg movement. Cushion 24 prevents bruising of the patient's legs. Support arm 21 may be provided with a plurality of receiving openings for adjusting the height of spindle 23.

Figure 2:
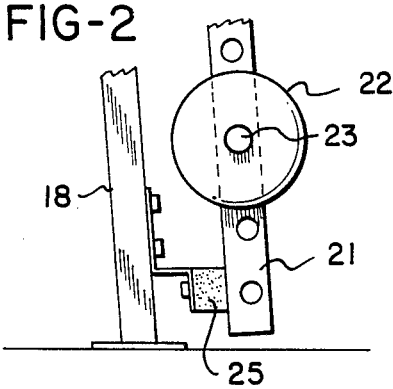
FIG. 2 illustrates apparatus for establishing a resting position for a leg loading assembly.

A rotation sensor 76 which may include a potentiometer of conventional design senses the rotation of support arm 21 and provides an electrical indication thereof to a stimulation console 27. As best illustrated in FIG. 2 a spacer member 25 mounted on the chair leg 18 (or 16) provides a predetermined rest position for the support arm.

Electrical stimulation of the quadriceps muscles is provided by four transcutaneous electrodes 28 mounted on the upper legs of the patient as illustrated in FIG. 1. Electrical stimulation signals of appropriate waveform are supplied to electrodes 28 by stimulation console 27 as hereinafter described in detail. The legs may be exercised alternately by alternate depression of switches 142, 143 mounted on chair arms 13 and 14. Depression of one of the switches 142, 143 causes stimulation console 27 to generate stimulation signals which produce gradual contraction and relaxation of the quadriceps muscles in an associated leg of the patient. The entire contraction and relaxation cycle may continue for a period of approximately ten seconds. During this period the leg raises and lowers the associated loading assembly 19 or 20.

Stimulation console 27 includes a power supply 50 designed as illustrated in FIG. 3A and connected for powering a first stimulator unit 53 configured as illustrated in FIG. 3B. A second power supply 51 powers a second stimulator unit 54 identical to stimulator unit 53. Each stimulator unit supplies stimulation signals to a pair of stimulation electrodes 28, 28. Either of stimulator units 53 or 54 may be triggered into initiating a leg lift cycle by momentary closure of one of switches 142, 143. Alternatively, stimulator units 53 and 54 may be triggered by an automatic switching unit 52. Either type of lift cycle triggering creates momentary pulses which are applied to stimulation units 53, 54 through optical isolation units 146 and 147. These optical isolation units are commercially purchased items comprising a light emitting diode and a phototransistor, as illustrated. Switching unit 52 is activated by closure of double pole-double throw switch 141.

Power supplies 50 and 51 are each powered by 115 volt, 60 cycle A.C. current supplied to transformers 101A and 101B. Transformers 101A and 101B convert the 115 volt supply current into a 6.3 volt drive and then step this 6.3 drive back up to 115 volts so as to isolate the high voltage stimulation drive from the outside supply current. An arrangement of diodes, resistors and capacitors, as illustrated, convert the isolated 115 volt supply into a 275 volt D.C. driving potential for application to switch 107. When switch 107 is closed the D.C. drive is supplied via line 205 to one of the transcutaneous electrodes 28. A stimulation driving circuit is then completed through the leg of the patient when the stimulator unit is triggered to produce conduction in a VMOS output transistor 92.

Power supplies 50 and 51 also include a third transformer 110 which produces a 24 volt A.C. signal for application across a rectifier bridge 111. The output from rectifier bridge 111 is utilized as illustrated in FIG. 3A to create +9 volt and −9 volt direct current power supplies for use by the stimulator units. A 9 volt battery is provided for powering switching unit 52 and the manually operated switches 142 and 143.

Switching unit 52 comprises a quad NAND gate connected to create a pair of inverters 124 and 125 by shorting the gate inputs. Inverter 124 produces a continuous square wave output comprising five second pulses repeated at a frequency of about six pulses per minute. The frequency of the square wave is controlled by the reactance of capacitor 126 and resistors 122 and 123. Resistor 122 is adjustable for variation of the frequency.

The square wave output from inverter 124 is applied to a pair of monostable multivibrators 130, 136 as identifed in TABLE I. Multivibrators 130 and 136 provide short duration pulses at the leading and trailing edges, respectively, of the above-mentioned square wave pulses. These short pulses are generated in alternating fashion by multivibrators 130 and 136 and have a duration which can be controlled by appropriate selection of capacitors 128 and 134 and resistors 129 and 135. For component values as listed in TABLE I the pulse width is about 0.3 seconds. Light emitting diodes 132 and 138 are provided to give a visual indication of trigger pulse generation. Trigger pulses from multivibrator 130 are applied via optical isolation unit 146 and line 206 to stimulation unit 53. Multivibrator 136 services stimulation unit 54 in a similar manner.

Stimulation unit 53 includes eight operational amplifiers 61 through 68 connected as illustrated in FIG. 3B. Amplifier 61 is triggered to the ON state by momentary closure of switch 229 or by generation of one of the above-mentioned pulses on line 206. Once triggered, operational amplifier 61 remains in the ON state for a period of time as determined by the resistance of resistor 71. For a resistance value as indicated in TABLE I and at a nominal mid-range resistance setting, the output waveform from amplifier 61 may be as generally illustrated by waveform 210 of FIG. 4. Amplifier 61 and its associated driving elements therefore comprise a timer operative to generate a timing signal which progresses from a level quiescent value to a timing pulse of adjustable duration and then back to the quiescent value.

Timing signal 210 is applied to the negative drive of reference integrator 62. This creates a reference signal which ramps upwardly from an initial or rest value to a working value and then downwardly back to the rest value as illustrated by signal 211 of FIG. 4. The slope of the upward ramp is controlled by the setting of resistor 72 while the slope of the downward ramp is controlled by the setting of resistor 73. A typical duration period from rest value through the upward and downward ramps and back to rest value is about eight seconds. The reference signal is used as a position reference for controlling the raising and lowering of the leg and hence controls the rate of limb extension, the time to hold a target angle and the rate of limb return.

Figure 4:
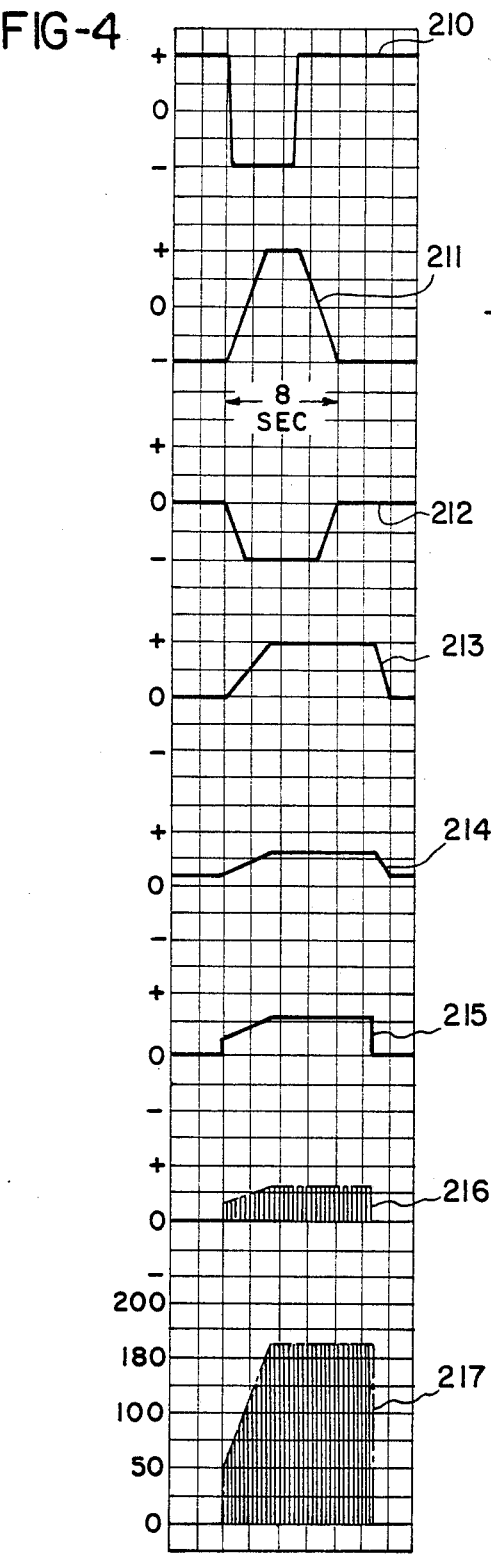
FIG. 4 is a schematic diagram illustrating signal waveforms as they appear without position sensor feedback at selected points in the circuitry of FIG. 3B.

During normal operation the reference signal produced by reference integrator 62 passes through switch 162 and potentiometer 74 to drive differential amplifier 63. A second input to the differential amplifier is supplied by rotation sensor 76. The output signal from differential amplifier 63 then is an error signal representing the difference between the actual leg position as measured by position sensor 76 and the desired position as indicated by the reference signal. Potentiometer 74 may be adjusted as desired to control the maximum voltage change of the reference signal during a contraction cycle and hence the target angle of limb extension. Another potentiometer 75 provides a balance adjustment to assure that the error signal is 0 during rest. Calibration of these potentiometers is accomplished as hereinafter described. Waveform 212 of FIG. 4 illustrates a resulting error signal when no patient is seated in chair 10, so that no feedback signal is generated by position sensor 76.

The error signal produced by differential amplifier 63 is applied to stimulus integrator 64, which is merely an operational amplifier connected for integrating the error signal. This integration produces a stimulation driving signal which is processed as hereinafter described for application to the stimulation electrodes. Thus there is provided a continuous, immediately reacting negative feedback system for control of leg position.

It is a feature of this invention that as the stimulated limb responds to a stimulation signal and achieves a desired position, the error signal becomes zero, but the stimulation driving signal holds a constant value for causing the limb to maintain its position. If the limb position exeeds the desired position as indicated by the reference signal, the output of differential amplifier 63 (error signal) becomes positive, and the output of stimulus integrator 64 (stimulation driving signal) is decreased. This causes lowering of the limb. Thus the limb tracks the reference signal without the jerky, hazardous limb movement which would occur if the error signal were used in raw form as a stimulation drive. Dampening of the stimulation drive may be controlled by adjustment of potentiometer 77. Waveform 213 of FIG. 4 illustrates a stimulation driving signal for open loop operation (response to an error signal as depicted by waveform 212).

Figure 5:
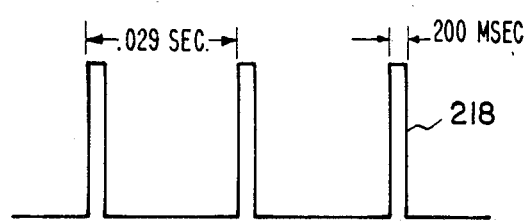
FIG. 5 illustrates the chopping signal applied to solid state switch 95.

Stimulator unit 53 also comprises an amplifier 67 connected for operation as a pulse generator. Pulse generator 67 generates a pulsed chopping signal comprising pulses which are substantially shorter in duration than the above-mentioned timing pulse. The duration of the chopping pulses is controlled by the combined resistance of variable resistor 80 and fixed resistor 202. For resistance values as set forth in TABLE I and a mid-range setting for resistor 80, the chopping pulses have a pulse width of about 200 microseconds. The frequency of the chopping pulses is controlled by the resistance of variable resistor 81 and fixed resistor 196. For resistance values as set forth in TABLE I and at a mid-range setting of variable resistor 81, chopping pulses are generated at a frequency of about 35 Hz. Thus the chopping signal may have a waveform as generally indicated by the waveform 218 of FIG. 5.

The chopping signal and the stimulation driving signal are both applied to a solid state switch 95. However, the stimulation driving signal passes through amplifier 66 and solid state switch 94 enroute to solid state switch 95. Switches 93 and 94 provide functions as hereinafter described, and amplifier 66 adjusts the level of the stimulation driving signal to provide a stimulator output above the stimulation threshold of the muscles being stimulated. The chopping signal controls the switching state of switch 95 while the stimulation driving signal is being applied thereto. This chops the stimulation driving signal into a pulsatile output signal characterized by pulses having the same frequency and duration as the chopping pulses. The pulsatile output signal is illustrated by waveform 216 of FIG. 4. Waveform 214 illustrates the stimulation driving signal after amplification by amplifier 66, and waveform 215 illustrates the signal modification produced by solid state switch 94.

During the contraction cycle solid state switch 94 is closed and solid state switch 93 is open; both switches being controlled by comparator 65 and transistor 91. Comparator 65 is connected to receive the reference signal generated by reference integrator 62. During the contraction cycle the reference signal remains positive, and this triggers comparator 65 for a positive output. The positive output from comparator 65 closes solid state switch 94 to permit application of the stimulation driving signal to solid state switch 95. Simultaneously transistor 91 is caused to open solid state switch 93 thereby permitting operation of stimulus integrator 64. Comparator 65 remains in the ON state so long as the reference signal remains positive and for about two seconds thereafter. After the reference signal has maintained a 0 value for two seconds (indicating a resting position for the leg) solid state switch 93 is closed, thereby zeroing the stimulation driving signal. Solid state switch 94 is opened at the same time. This assures that the leg comes smoothly to rest before the stimulation is terminated.

As described above the stimulation driving signals are amplified by amplifier 66 and thereafter chopped by state switch 95 to create a pulsatile output signal. This latter signal drives a voltage follower 68 which in turn drives high voltage output transistor 92. Conduction of transistor 92 provides a path to ground for its associated transcutaneous electrode 28, so that stimulation of the leg muscles is enabled. Current flow through transistor 92 is limited to about 150 milliamperes. Waveform 217 illustrates a resulting stimulator signal appearing across the stimulation electrodes 28, 28.

Calibration of potentiometers 74 and 75 is carried out prior to stimulation of the patient's muscles. This is accomplished with switch 163 in the UP position as illustrated in FIG. 3B and switch 162 initially in the operating or DOWN position. With limb loading assembly 20 in the rest position against spacer member 25, the error signal from differential amplifier 63 is read on voltmeter 184. At this time potentiometer 75 is adjusted to produce a balanced condition (zero reading on voltmeter 184). After this has been accomplished, switch 162 is put into the UP position to generate a calibration signal simulating a reference signal calling for maximum leg extension. Limb loading assembly 20 is then raised to the desired maximum angle of limb extension. Potentiometer 76 generates a feedback signal corresponding to this position. Differential amplifier reads this feedback signal and the above-mentioned calibration signal and generates a corresponding difference (or error) signal. Potentiometer 74 is then adjusted to reduce that signal to zero. The procedure is repeated for the other limb loading assembly, after which switches 162 are returned to their operating positions and an exercise routine may be commenced. No stimulation is applied to the legs during this calibration procedure. During such exercise the patient's legs are stimulated to raise to the angles established during the above-mentioned calibration procedure.

The minimal or threshold stimulation is adjusted by adjustment of potentiometer 79. Push button switch 164 allows adjustment of the threshold stimulation prior to initiation of a contraction cycle. At this time switch 164 is closed and potentiometer 79 is adjusted until the leg muscles begin to twitch without movement of the limb. A voltmeter 184 is provided for monitoring either the error signal or the stimulation driving signal. A switch 163 is provided for selection of the signal to be monitored. Potentiometer 78 permits adjustment of the maximum stimulation drive. (Typically limited to about 150 milliamperes).

It is apparent that the above-described exercising apparatus could be used in different forms for exercising either legs or arms. Thus a position sensor may readily be strapped on a paralyzed limb so as to measure the joint rotation and provide a position signal indicative thereof. Dynamic loading may be supplied by securing a simple weight to the limb.

While the form of apparatus herein described constitutes a preferred embodiment of this invention, it is to be understood that the invention is not limited to this precise form of apparatus, and that changes may be made therein without departing from the scope of the invention which is defined in the appended claims.

TABLE I

| Ref. No. | Identification |
| --- | --- |
| 61–68 | ¼ LM 324 quad. op. amp. |
| 71 | 2 Meg. Ω variable |
| 72, 73 | 1 Meg. Ω variable |
| 74–76 | 100K Ω variable |
| 77 | 2 Meg. Ω variable |
| 78, 79 | 100K Ω variable |
| 80 | 5K Ω variable |
| 81 | 500K Ω variable |
| 91 | 2N2222 |
| 92 | IRF 433 |
| 93–95 | ⅓ 4066 |
| 102 | 100 Ω |
| 105, 106 | 220K Ω |
| 108, 109 | 500 μf |
| 111 | BR1 |
| 112, 113 | 100 Ω |
| 114, 115 | 1000 μf |
| 116 | 7808 + 8 V regulator |
| 117 | 7908 − 8 V regulator |
| 122 | 500K Ω variable |
| 123 | 470K Ω |
| 124, 125 | ½ 4011 quad. NAND Gate |
| 126 | 10 μf |
| 127 | 1 Meg. Ω |
| 128 | 0.033 μf |
| 129 | 9.1 Meg. Ω |
| 130 | 4528 monostable multivibrator |
| 133 | 3.3K Ω |
| 134 | 0.033 μf |
| 135 | 9.1 Meg. Ω |
| 136 | 4528 monostable multivibrator |
| 139 | 3.3K Ω |
| 140 | 0.033 μf |
| 144, 145 | 15K Ω |
| 146, 147 | 4N33 opto isolator |
| 148 | 150K Ω |
| 149 | 220K Ω |
| 150 | 10K Ω |
| 151 | 10K Ω |
| 152 | 0.1 μf |
| 153 | 2 μf |
| 154 | 220K Ω |
| 172 | 220K Ω |
| 173 | 10K Ω |
| 174 | 5 μf |
| 175 | 6.8 Meg. Ω |
| 176 | 2.2 Meg. Ω |
| 177 | 2.2 Meg. Ω |
| 178 | 10 Meg. Ω |
| 179 | 10 Meg. Ω |
| 180 | 220K μ |
| 181 | 5 μf |
| 182 | 68K Ω |
| 183 | 330K Ω |
| 185 | 220K Ω |
| 186 | 150K Ω |
| 187 | 1.5 Meg. Ω |
| 188 | 0.47 μf |
| 189 | 10K Ω |
| 190 | 1 Meg. Ω |
| 191 | 10K Ω |
| 192 | 100K Ω |
| 193 | 0.022 μf |
| 194 | 100K Ω |
| 195 | 100K Ω |
| 196 | 680K Ω |
| 198 | 100K Ω |
| 199 | 1 Meg. Ω |
| 200 | 68K Ω |
| 201 | 100K Ω |
| 202 | 1.5K Ω |

What is claimed is:

1. Apparatus for stimulating a paralyzed human limb to move from a rest position to a working position and thence back to a rest position comprising:
    means for generating a reference signal indicating desired limb positions varying continuously from said rest position to said working position and thence back to said rest position,
    a position sensor for sensing the position of said limb and generating a position signal corresponding thereto,
    a differential amplifier for generating an error signal representing the difference between said reference signal and said position signal,
    a stimulus integrator for integrating said error signal to produce a stimulation driving signal,
    electrode means responsive to said stimulation driving signal for stimulating muscular activity in said limb and causing aforesaid movement, and
    dynamic load means for generating a force to resist said movement and cause muscular exertion in said limb.

2. Apparatus according to claim 1 wherein said first named means comprises a timer for generating a timing signal characterized by a level quiescent value and a timing pulse of predetermined duration, and a reference integrator for integrating said timing signal to produce said reference signal.

3. Apparatus for cyclically stimulating a paralyzed human limb to move from a rest position to a working positiion and thence back to said rest position comprising:
    a timer for generating a timing signal characterized by a level quiescent value and a timing pulse of predetermined duration,
    a reference integrator for integrating said timing signal to produce a reference signal which ramps from a rest value to a working value and then reversely to said rest value,
    a position sensor for generating a position signal corresponding to the position of said limb,
    a differential amplifier for generating an error signal representing the difference between said reference signal and said position signal,
    a stimulus integrator for integrating said error signal to produce a stimulation driving signal,
    chopping means for converting said stimulation driving signal into a pulsatile output signal characterized by pulses which are substantially shorter in duration than said timing pulse,
    electrode means responsive to said output signal for stimulating muscular activity in said limb and causing aforesaid movement, and
    dynamic load means for generating a force to resist said movement and cause muscular exertion in said limb.

4. Apparatus according to claim 3 wherein said chopping means comprises solid state switch, means for applying said stimulation driving signal to said solid state switch, a pulse generator for generating switching pulses having the frequency and duration of the pulses characterizing said pulsatile output signal, and means for causing said solid state switch to chop said stimulation driving signal in accordance with variations in said switching pulses.

5. Apparatus according to claim 4 and further comprising means for selectively applying to said differential amplifier a calibration signal simulating said reference signal as it appears when said limb is at said working position and means for zeroing the output from said differential amplifier when said calibration signal is so applied.

6. Apparatus according to claim 4 and further comprising means operable after a predetermined time following return of said reference signal to said rest value for zeroing said stimulation driving signal and terminating generation of said pulsatile output signal.

7. Apparatus for exercising both legs of a paralyzed person comprising:

a chair for seating of said person, a pair of weighted loading assemblies pivotally supported by said chair for dynamically opposing lifting motion of said legs, and a pair of stimulator units for alternately stimulating said legs to extend upwardly against the resisting action of said loading assemblies, each of said stimulation units comprising:

a timer for generating a timing signal characterized by a level quiescent value and a timing pulse of predetermined duration, a reference integrator for integrating said timing signal to produce a reference signal which ramps from a rest value to a working value and then reversely to said rest value, a position sensor for generating a position signal corresponding to the position of a leg being stimulated, a differential amplifier for generating an error signal representing the difference between said reference signal and said position signal, a stimulus integrator for integrating said error signal to produce a stimulation driving signal, a pulse generator for generating a switching signal comprising switching pulses which are substantially shorter in duration than said timing pulse, switching means for chopping said stimulation driving signal in accordance with variations in said switching pulses to produce a pulsatile output signal, and electrode means responsive to said output signal for stimulating muscular activity in said leg and causing movement thereof.

8. Apparatus according to claim 7 each of said timers comprising means to cause generation of said timing signal in response to a momentary input signal.

9. Apparatus according to claim 8 further comprising an automatic switching unit for generating said momentary input signals and means for alternately applying said momentary signals to said stimulation units.

10. Apparatus according to claim 8 further comprising switches mounted on said chair for manual generation of said momentary signals and means for applying said momentary input signals to said stimulation units.

* * * * *